(12) United States Patent
Bookbinder et al.

(10) Patent No.: US 9,708,216 B2
(45) Date of Patent: Jul. 18, 2017

(54) PHOSPHOROUS CONTAINING GLASS HAVING ANTIMICROBIAL EFFICACY

(71) Applicant: CORNING INCORPORATED, Corning, NY (US)

(72) Inventors: Dana Craig Bookbinder, Corning, NY (US); Nicholas Francis Borrelli, Elmira, NY (US); Matthew John Dejneka, Corning, NY (US); Timothy Michael Gross, Corning, NY (US)

(73) Assignee: CORNING INCORPORATED, Corning, NY (US)

( * ) Notice: Subject to any disclaimer, the term of this patent is extended or adjusted under 35 U.S.C. 154(b) by 166 days.

(21) Appl. No.: 14/548,650

(22) Filed: Nov. 20, 2014

(65) Prior Publication Data

US 2015/0147576 A1 May 28, 2015

Related U.S. Application Data

(60) Provisional application No. 61/908,828, filed on Nov. 26, 2013.

(51) Int. Cl.
  *C03C 21/00* (2006.01)
  *C03C 3/097* (2006.01)
  (Continued)

(52) U.S. Cl.
  CPC ............ *C03C 21/005* (2013.01); *A01N 59/00* (2013.01); *A01N 59/16* (2013.01); *C03C 3/097* (2013.01);
  (Continued)

(58) Field of Classification Search
  None
  See application file for complete search history.

(56) References Cited

U.S. PATENT DOCUMENTS 3,357,876 A * 12/1967 Rinehart ................. C03C 3/097
                                                              252/193
4,055,703 A    10/1977 Rinehart
                      (Continued)

FOREIGN PATENT DOCUMENTS

JP         01167245     6/1989    ............. C03B 27/02
WO         2006058906   6/2006

OTHER PUBLICATIONS

Nunzio, Brovarone, Spriano, Milanese, Verne, Bergo, Maina, Spinelli, "Silver containing bioactive glasses prepared by molten salt ion-exchange", Journal of the European Ceramic Society, 24 (2004) 2935-2942.

(Continued)

*Primary Examiner* — David Sample
(74) *Attorney, Agent, or Firm* — Jie Gao (57) ABSTRACT

A strengthened antimicrobial glass including greater from about 50.0 mol. % to about 65.0 mol. % $SiO_2$, about 14.0 mol. % to about 22.0 mol. % $Al_2O_3$, about 14.0 mol. % to about 22.0 mol. % $R_2O$, wherein R is an alkali metal, and about 4.0 mol. % to 10.0 mol. % $P_2O_5$. The glass may have a compressive stress layer having a thickness of greater than or equal to about 20 μm to less than or equal to about 60 μm and having a compressive stress of greater than or equal to about 700 MPa. The glass may have an antimicrobial activity greater than or equal to about 1.0 log kill at about 23° C. and about 40.0% relative humidity. A method for making the glass may include obtaining a glass article, strengthening the glass article by contact with a first ion-exchange liquid, and contacting the glass article with second ion-exchange liquid comprising an antimicrobial agent.

20 Claims, 2 Drawing Sheets

(51) Int. Cl.
    *C03C 4/00*     (2006.01)
    *A01N 59/00*     (2006.01)
    *A01N 59/16*     (2006.01)
    *C03C 17/30*     (2006.01)

(52) U.S. Cl.
    CPC ............... *C03C 4/00* (2013.01); *C03C 17/30* (2013.01); *C03C 21/002* (2013.01); *C03C 2204/02* (2013.01); *Y10T 428/315* (2015.01); *Y10T 428/31612* (2015.04)

(56) References Cited

U.S. PATENT DOCUMENTS

| | | | |
|---|---|---|---|
| 7,232,777 B1 | 6/2007 | Van Hyning | |
| 8,973,401 B2 | 3/2015 | Borrelli et al. | |
| 9,156,724 B2 | 10/2015 | Gross | |
| 2009/0197048 A1 | 8/2009 | Amin et al. | 428/142 |
| 2011/0294648 A1 | 12/2011 | Chapman et al. | 501/63 |
| 2012/0034435 A1 | 2/2012 | Borrelli et al. | 428/210 |
| 2013/0122284 A1 | 5/2013 | Gross | 428/336 |
| 2013/0122313 A1* | 5/2013 | Gross | C03C 3/04 428/428 |
| 2014/0356605 A1* | 12/2014 | Adib | C03C 21/001 428/220 |
| 2014/0370302 A1* | 12/2014 | Amin | C03C 21/005 428/426 |
| 2014/0370303 A1* | 12/2014 | Jin | C03C 21/005 428/426 |
| 2015/0225287 A1* | 8/2015 | Amin | C03C 21/002 428/410 |
| 2015/0225288 A1* | 8/2015 | Bookbinder | C03C 21/005 428/410 |
| 2015/0239777 A1* | 8/2015 | Mauro | C03C 21/005 428/410 |

OTHER PUBLICATIONS

LV et al; "Antibiotic Glass Slide Coated With Silver Nanoparticles and Its Antimicrobial Capabilities"; Polym. Adv. Technol. 2008; 19: 1455-1460.

Verne et al; "Surface Silver-Doping of Biocompatible Glass to Induce Antibacterial Properties. Part I: Massive Glass"; J. Mater. Sci.: Mater. Med. (2009) 20: 733-740.

* cited by examiner

PHOSPHOROUS CONTAINING GLASS HAVING ANTIMICROBIAL EFFICACY

This application claims the benefit of priority under 35 U.S.C. §119 of U.S. Provisional Application Ser. No. 61/908,828 filed on Nov. 26, 2013 the content of which is relied upon and incorporated herein by reference in its entirety.

BACKGROUND

Field

The present disclosure is directed to phosphorous containing glass having antimicrobial efficacy and methods of making such glass. In particular, the disclosure is directed to a transparent, chemically strengthened glass with antimicrobial properties that may have a functional coating on the glass that does not interfere with the antimicrobial efficacy of the glass.

Technical Background

Recently, the use both metallic silver particles and silver salts have been described in the patent and technical literature as a means for imparting antibacterial properties to a variety of materials. Silver ions interact with a wide range of molecular processes within microorganisms resulting in a range of effects from inhibition of growth and loss of infectivity to cell death (cytotoxicity). The mechanism depends on both the concentration of silver ions that are present and the sensitivity of the microbial species to the silver ions. Contact time, temperature, pH and the presence of free water all impact both the rate and extent of antimicrobial activity.

The prevalence of "touch screens" in contemporary society gives rise to many surfaces that can harbor microbes, bacteria and viruses, and these microbes can be transferred from person to person. Antimicrobial activity at high relative humidity and physiological temperatures (e.g., about 37° C.) is achievable. However, at ambient conditions (e.g., about 42% relative humidity and about 23° C.) the efficacy of silver ions decreases. Accordingly, a need exists for a glass that has improved efficacy of silver ions at ambient conditions.

SUMMARY

In embodiments, a strengthened antimicrobial glass is disclosed. The glass may include greater than or equal to about 50.0 mol. % to less than or equal to about 65.0 mol. % $SiO_2$, greater than or equal to about 14.0 mol. % to less than or equal to about 22.0 mol. % $Al_2O_3$, greater than or equal to about 14.0 mol. % to less than or equal to about 22.0 mol. % $R_2O$, wherein R is an alkali metal, and greater than or equal to about 4.0 mol. % to less than or equal to about 10.0 mol. % $P_2O_5$. The glass may have a compressive stress layer that has a thickness of greater than or equal to about 20 µm to less than or equal to about 60 µm, and a compressive stress of greater than or equal to about 700 MPa. The glass may also have an antimicrobial activity greater than or equal to about 1.0 Log Kill at about 23° C. and about 40.0% relative humidity.

In embodiments, a method for making strengthened antimicrobial glass is disclosed. The method may include obtaining a glass article having greater than or equal to about 50.0 mol. % to less than or equal to about 65.0 mol. % $SiO_2$, greater than or equal to about 14.0 mol. % to less than or equal to about 22.0 mol. % $Al_2O_3$, greater than or equal to about 14.0 mol. % to less than or equal to about 22.0 mol. % $R_2O$, wherein R is an alkali metal, and greater than or equal to about 4.0 mol. % to less than or equal to about 10.0 mol. % $P_2O_5$. The glass article may be strengthened by contact with a first ion-exchange liquid; and subsequently contacted with a second ion-exchange liquid comprising an antimicrobial agent. The glass may have a compressive stress layer having a thickness of greater than or equal to about 20 µm to less than or equal to about 60 µm, and a compressive stress of greater than or equal to about 700 MPa. The glass may have an antimicrobial activity greater than or equal to about 1.0 log kill at about 23° C. and a relative humidity of about 40%.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Embodiments disclosed herein are directed to phosphorous containing glasses having antimicrobial efficacy and methods for making such glasses. In embodiments, The glass may include greater than or equal to about 50.0 mol. % to less than or equal to about 65.0 mol. % $SiO_2$, greater than or equal to about 14.0 mol. % to less than or equal to about 22.0 mol. % $Al_2O_3$, greater than or equal to about 14.0 mol. % to less than or equal to about 22.0 mol. % $R_2O$, wherein R is an alkali metal, and greater than or equal to about 4.0 mol. % to less than or equal to about 10.0 mol. % $P_2O_5$. The glass may have a compressive stress layer that has a thickness of greater than or equal to about 20 µm to less than or equal to about 60 µm, and a surface compressive stress of greater than or equal to about 700 MPa. The glass may also have an antimicrobial activity greater than or equal to about 1.0 Log Kill at about 23° C. and about 40.0% relative humidity. Methods for making such glass articles are also disclosed in embodiments.

Glass Composition

In an exemplary glass composition, $SiO_2$ is the largest constituent and, as such, $SiO_2$ is the primary constituent of the glass network formed from the glass composition. Pure $SiO_2$ has a relatively low CTE. However, pure $SiO_2$ has a high melting point. Accordingly, if the concentration of $SiO_2$ in the glass composition is too high, the formability of the glass composition can be diminished as higher concentrations of $SiO_2$ increase the difficulty of melting the glass, which, in turn, adversely impacts the formability of the glass. Low $SiO_2$ glasses, such as, for example, glass with less than 50 mol. % $SiO_2$, tend to have poor durability and resistance to devitrification, so it is practical to have more than 50 mol. % $SiO_2$ for ease of forming.

In embodiments, the glass composition can comprise $SiO_2$ in a concentration from greater than or equal to about 50 mol. % to less than or equal to about 65 mol. %, such as from greater than or equal to about 52 mol. % to less than or equal to about 63 mol. %. In other embodiments, the glass composition can comprise $SiO_2$ in a concentration from greater than or equal to about 55 mol. % to less than or equal to about 60 mol. %, such as from greater than or equal to about 57 mol. % to less than or equal to about 58 mol. %.

The glass composition of embodiments can further comprise $Al_2O_3$ in addition to $SiO_2$. $Al_2O_3$ can serve as a glass network former, similar to $SiO_2$. $Al_2O_3$ can increase the viscosity of the glass composition. However, when the concentration of $Al_2O_3$ is balanced against the concentration of $SiO_2$ and, optionally, the concentration of alkali oxides in the glass composition, $Al_2O_3$ can reduce the liquidus temperature of the glass melt, thereby enhancing the liquidus viscosity and improving the compatibility of the glass composition with certain forming processes. In addition, $Al_2O_3$ can enhance the ion exchange performance of alkali silicate glasses.

In embodiments, the glass composition can comprise $Al_2O_3$ in a concentration from greater than or equal to about 14 mol. % to less than or equal to about 22 mol. %, such as from greater than or equal to about 15 mol. % to less than or equal to about 20 mol. %. In other embodiments, the glass composition can comprise $Al_2O_3$ in a concentration from greater than or equal to about 16 mol. % to less than or equal to about 19 mol. %, such as from greater than or equal to about 17 mol. % to less than or equal to about 18 mol. %.

Alkali metal oxides (hereinafter referred to as "$R_2O$" where "R" is one or more alkali metals) may be added to lower the viscosity of a glass to improve the meltability and the formability thereof. In addition, alkali metal oxides may also enable ion exchange that modifies both the stress and refractive index profiles of the glass. When the content of $R_2O$ is too large, the thermal expansion coefficient of the glass becomes too large, and the thermal shock resistance of the glass may decrease. In embodiments, the glass composition may include one or more of $Li_2O$, $Na_2O$, $K_2O$, $Rb_2O$, and $Cs_2O$ as an alkali metal oxide. In some embodiments, the glass composition may include $Na_2O$ and/or $Li_2O$ as alkali metal oxides. In other embodiments, the glass composition may include $Na_2O$ as an alkali metal oxide. In some embodiments, the glass composition do not contain $Li_2O$ or lithium from any other source.

In embodiments, the glass composition can comprise $R_2O$ in a concentration from greater than or equal to about 14 mol. % to less than or equal to about 22 mol. %, such as from greater than or equal to about 15 mol. % to less than or equal to about 20 mol. %. In other embodiments, the glass composition can comprise $R_2O$ in a concentration from greater than or equal to about 16 mol. % to less than or equal to about 19 mol. %, such as from greater than or equal to about 17 mol. % to less than or equal to about 18 mol. %.

Including a relatively high amount of $R_2O$ in the glass composition may allow enhanced ionic interdiffusion of small alkali metal ions and large alkali metal ions during standard ion exchange processes (e.g., ion exchange in a molten $KNO_3$ salt bath at about 410° C.). Without being constrained to any particular theory, it is believed that the relatively high amount of $R_2O$ may act as a charge compensator for $Al^{3+}$, thereby forming charge balanced units tetrahedrally coordinated with oxygen.

To retain high indentation damage resistance, glass compositions according to embodiments have a molar ratio of $Al_2O_3$ to $R_2O$ of from greater than or equal to about 0.5:1 to less than or equal to about 1.5:1.0, such as about 1.0:1.0. However, in embodiments where glass compositions are required to have high amounts of $R_2O$ and a ratio of $Al_2O_3$ to $R_2O$ of, for example, about 1:1, the balance of $SiO_2$ may not be sufficient to make the glass composition compatible with zircon forming bodies at the forming temperature, potentially leading to the formation of zircon defects in the glass.

However, $P_2O_5$ may increase the zircon breakdown temperature. Accordingly, in embodiments, $P_2O_5$ may be substituted for $SiO_2$ to increase the zircon breakdown temperature and allow glass compositions with high $R_2O$ contents and an $Al_2O_3$ to $R_2O$ ratio of, for example, about 1:1, to be compatible with zircon forming bodies. Without being constrained to any particular theory, it is believed that the 35 kP temperature decreases and the zircon breakdown increases as the molar percentage of $SiO_2$ decreases and the molar percentage of $P_2O_5$ increases.

In embodiments, the glass composition can comprise $P_2O_5$ in a concentration from greater than or equal to about 4.0 mol. % to less than or equal to about 10 mol. %, such as from greater than or equal to about 5.0 mol. % to less than or equal to about 9.0 mol. %. In other embodiments, the glass composition can comprise $P_2O_5$ in a concentration from greater than or equal to about 6.0 mol. % to less than or equal to about 8.0 mol. %, such as about 7.0 mol. %.

The glass composition can, in some embodiments, contain other elements, such as alkaline earth metal oxides. In embodiments, the alkaline earth metal oxides can be selected from MgO, CaO, SrO, BaO, and combinations thereof. These oxides can be added to increase meltability, durability, and glass stability. In addition, alkaline earth metal oxides can be added as stabilizers that help prevent degradation of the glass composition upon exposure to environmental conditions. While ZnO is not an alkaline earth, it is a divalent oxide and serves a similar function as the above referenced alkaline earth metal oxides and, thus, ZnO can be added to the glass composition to enhance the same properties as alkaline earth metal oxides. However, adding too much alkaline earth metal oxide and/or ZnO to the glass composition can decrease its formability.

In embodiments, the glass composition comprises alkaline earth metal oxide in concentrations from greater than or equal to 0.0 mol. % to less than or equal to about 4.0 mol. %, such as from greater than or equal to about 1.0 mol. % to less than or equal to about 3.0 mol. %. In other embodiments, the glass composition comprises alkaline earth metal oxides in concentrations from greater than or equal to about 1.5 mol. % to less than or equal to about 2.5 mol. %. Similarly, in embodiments, the glass composition comprises ZnO in concentrations from greater than or equal to 0.0 mol. % to less than or equal to about 4.0 mol. %, such as from greater than or equal to about 1.0 mol. % to less than or equal to about 3.0 mol. %. In other embodiments, the glass composition comprises ZnO in concentrations from greater than or equal to about 1.5 mol. % to less than or equal to about 2.5 mol. %.

In embodiments, the glass composition can comprise fining agents, such as, for example, $SnO_2$, sulfates, chlorides, bromides, $Sb_2O_3$, $As_2O_3$, and $Ce_2O_3$. In embodiments, the glass composition can comprise fining agents in concentrations from greater than or equal to 0.0 mol. % to less than or equal to about 1.0 mol. %, such as from greater than or equal to about 0.002 mol. % to less than or equal to about 0.9 mol. %. In other embodiments, the glass composition can comprise fining agents in concentrations from greater than or equal to about 0.05 mol. % to less than or equal to about 0.8 mol. %, such as from greater than or equal to about 0.1 mol. % to less than or equal to about 0.7 mol. %. In yet other embodiments, the glass composition can comprise fining agents in concentrations from greater than or equal to about 0.1 mol. % to less than or equal to about 0.3 mol. %, such as about 0.15 mol. %. In embodiments that use sulfates as the fining agents, the sulfates can be included in amount from greater than or equal to about 0.001 mol. % to less than or equal to about 0.1 mol. %.

Accordingly, in some embodiments, the glass composition may comprise greater than or equal to about 50.0 mol. % to less than or equal to about 65.0 mol. % $SiO_2$, greater than or equal to about 14.0 mol. % to less than or equal to about 22.0 mol. % $Al_2O_3$, greater than or equal to about 14.0 mol. % to less than or equal to about 22.0 mol. % $R_2O$, and greater than or equal to about 4.0 mol. % to less than or equal to about 10.0 mol. % $P_2O_5$. It should be understood that all molar percentages within the above ranges are envisioned and included in this disclosure.

Specific glass compositions according to embodiments are in Table 1 below.

TABLE 1

| Example | 1 | 2 | 3 | 4 | 5 | 6 | 7 | 8 | 9 |
|---|---|---|---|---|---|---|---|---|---|
| $SiO_2$ mol % | 52 | 54 | 56 | 58 | 50 | 60 | 58 | 60 | 56 |
| $B_2O_3$ | 4 | 0 | 0 | 0 | 0 | 0 | 5 | 4 | 2 |
| $Al_2O_3$ | 22 | 23 | 22 | 21 | 27 | 20 | 16 | 16 | 20 |
| $P_2O_5$ | 6 | 7 | 6 | 5 | 7 | 4 | 5 | 4 | 4 |
| $Na_2O$ | 14 | 14 | 14 | 14 | 14 | 14 | 14 | 14 | 14 |
| $K_2O$ | 2 | 2 | 2 | 2 | 2 | 2 | 2 | 2 | 2 |
| $As_2O_3$ | 0 | 0 | 0 | 0 | 0 | 0 | 0 | 0 | 0 |
| $Cs_2O$ | 0 | 0 | 0 | 0 | 0 | 0 | 0 | 0 | 0 |
| $Li_2O$ | 0 | 0 | 0 | 0 | 0 | 0 | 0 | 0 | 0 |
| MgO | 0 | 0 | 0 | 0 | 0 | 0 | 0 | 0 | 0 |
| ZnO | 0 | 0 | 0 | 0 | 0 | 0 | 0 | 0 | 0 |
| $SnO_2$ | 0 | 0 | 0 | 0 | 0 | 0 | 0 | 0 | 0 |
| $ZrO_2$ | 0 | 0 | 0 | 0 | 0 | 0 | 0 | 0 | 0 |
| CaO | | | | | | | | | |
| $P_2O_5 + R_2O/Al_2O_3 + B_2O_3$ | 1.18182 | 1 | 1 | 1 | 0.85185 | 1 | 1 | 1 | 0.90909 |
| $Al_2O_3 + B_2O_3/R_2O$ | 1.625 | 1.438 | 1.375 | 1.313 | 1.6875 | 1.25 | 1.313 | 1.25 | 1.375 |
| Density (g/cm³) Archimedes | 2.3915 | 2.424 | 2.397 | 2.408 | | 2.42 | 2.379 | 2.368 | 2.4006 |
| Molar Volume (cm³/mol) | 31.59 | 31.52 | 31.36 | 30.7 | | 30.04 | 30.39 | 30.15 | 30.36 |
| Calc Young's Modulus (GPa) Makashima MacKenzie | 80.5 | | | | | | | | |
| Young's Modulus RUS (GPa) | | | | | 69.2 | | | 63.91 | |
| Shear Mudulus RUS (GPa) | | | | | 28.4 | | | 26.13 | |
| Poissons Ratio RUS | | | | | 0.217 | | | 0.223 | |
| Pre-IX Vickers Crack Initiation Load (gf) | 1000-2000 | | | | 1000-2000 | | 1000-2000 | | |
| DSC Glass Transition Temperature (° C.) | | | | | | | | | |
| CTE (10^-7) (1/K) | | | | | | | | | |
| Liquidus Temperature (° C.) | | >1250 | >1250 | 930 | | 750 | 775 | 770 | 775 |

| Example | 10 | 11 | 12 | 13 | 14 | 15 | 16 | 17 | 18 |
|---|---|---|---|---|---|---|---|---|---|
| $SiO_2$ mol % | 59 | 60 | 59.9 | 59.9 | 59.9 | 60 | 62 | 62 | 58 |
| $B_2O_3$ | 1 | 0 | 4 | 4 | 4 | 4.5 | 2.5 | 4.5 | 4.5 |
| $Al_2O_3$ | 20 | 20 | 16 | 16 | 16 | 15.5 | 15.5 | 15.5 | 17.5 |
| $P_2O_5$ | 4 | 4 | 4 | 4 | 4 | 4 | 4 | 4 | 4 |
| $Na_2O$ | 14 | 14 | 15.5 | 15.5 | 15.5 | 15.5 | 15.5 | 13.5 | 15.5 |
| $K_2O$ | 2 | 2 | 0.5 | 0.5 | 0.5 | 0.5 | 0.5 | 0.5 | 0.5 |
| $As_2O_3$ | 0 | 0 | 0 | 0 | 0 | 0 | 0 | 0 | 0 |
| $Cs_2O$ | 0 | 0 | 0 | 0 | 0 | 0 | 0 | 0 | 0 |
| $Li_2O$ | 0 | 0 | 0 | 0 | 0 | 0 | 0 | 0 | 0 |

TABLE 1-continued

| | | | | | | | | | |
|---|---|---|---|---|---|---|---|---|---|
| MgO | 0 | 0 | 0 | 0 | 0 | 0 | 0 | 0 | 0 |
| ZnO | 0 | 0 | 0 | 0 | 0 | 0 | 0 | 0 | 0 |
| $SnO_2$ | 0 | 0 | 0.1 | 0.1 | 0.1 | 0 | 0 | 0 | 0 |
| $ZrO_2$ | 0 | 0 | 0.02 | 0.02 | 0.02 | 0 | 0 | 0 | 0 |
| CaO | | | | | | | | | |
| $P_2O_5 + R_2O/$ $Al_2O_3 + B_2O_3$ | 0.95238 | 1 | 1 | 1 | 1 | 1 | 1.11111 | 0.9 | 0.90909 |
| $Al_2O_3 + B_2O_3/$ $R_2O$ | 1.3125 | 1.3 | 1.25 | 1.25 | 1.25 | 1.25 | 1.125 | 1.42857 | 1.375 |
| Density (g/cm³) Archimedes | 2.3917 | | | | | | 2.391 | 2.363 | 2.386 |
| Molar Volume (cm³/mol) | 30.43 | | | | | | 29.51 | 29.92 | 30 |
| Calc Young's Modulus (GPa) Makashima MacKenzie | 80.5 | | | | | | | | |
| Young's Modulus RUS (GPa) | | | | 63 | 63 | | | | |
| Shear Mudulus RUS (GPa) | | | | 25 | 25.9 | | | | |
| Poissons Ratio RUS | | | | 0.21 | 0.21 | | | | |
| Pre-IX Vickers Crack Initiation Load (gf) | | | | | | | | | |
| DSC Glass Transition Temperature (° C.) | | | | | | | | | |
| CTE (10^-7) (1/K) | | | | | | | | | |
| Liquidus Temperature (° C.) | 780 | | | | 790 | 780 | | | |

| Example | 19 | 20 | 21 | 22 | 23 | 24 | 25 | 26 | 27 |
|---|---|---|---|---|---|---|---|---|---|
| $SiO_2$ mol % | 58 | 58 | 58 | 60 | 60 | 60 | 60 | 60 | 60 |
| $B_2O_3$ | 6.5 | 4.5 | 4.5 | 2.5 | 4.5 | 6.5 | 2.5 | 2.5 | 4.5 |
| $Al_2O_3$ | 15.5 | 16 | 15.5 | 17.5 | 17.5 | 15.5 | 15.5 | 15.5 | 15.5 |
| $P_2O_5$ | 4 | 6 | 4 | 4 | 4 | 4 | 6 | 4 | 6 |
| $Na_2O$ | 15.5 | 16 | 17.5 | 15.5 | 13.5 | 13.5 | 15.5 | 17.5 | 13.5 |
| $K_2O$ | 0.5 | 0.5 | 0.5 | 0.5 | 0.5 | 0.5 | 0.5 | 0.5 | 0.5 |
| $As_2O_3$ | 0 | 0 | 0 | 0 | 0 | 0 | 0 | 0 | 0 |
| $Cs_2O$ | 0 | 0 | 0 | 0 | 0 | 0 | 0 | 0 | 0 |
| $Li_2O$ | 0 | 0 | 0 | 0 | 0 | 0 | 0 | 0 | 0 |
| MgO | 0 | 0 | 0 | 0 | 0 | 0 | 0 | 0 | 0 |
| ZnO | 0 | 0 | 0 | 0 | 0 | 0 | 0 | 0 | 0 |
| $SnO_2$ | 0 | 0 | 0 | 0 | 0 | 0 | 0 | 0 | 0 |
| $ZrO_2$ | 0 | 0 | 0 | 0 | 0 | 0 | 0 | 0 | 0 |
| CaO | | | | | | | | | |
| $P_2O_5 + R_2O/$ $Al_2O_3 + B_2O_3$ | 0.90909 | 1.1 | 1.1 | 1 | 0.81818 | 0.81818 | 1.22222 | 1.22222 | 1 |
| $Al_2O_3 + B_2O_3/$ $R_2O$ | 1.375 | 1.3 | 1.11111 | 1.25 | 1.57143 | 1.57143 | 1.125 | 1 | 1.42857 |
| Density (g/cm³) Archimedes | | | | 2.39 | 2.372 | 2.356 | 2.384 | 2.411 | 2.359 |
| Molar Volume (cm³/mol) | | | | 29.8 | 30.16 | 30.09 | 30.28 | 29.28 | 30.67 |
| Calc Young's Modulus (GPa) Makashima MacKenzie | | | | | | | | | |
| Young's Modulus RUS (GPa) | | | | | | | | | |
| Shear Mudulus RUS (GPa) | | | | | | | | | |
| Poissons Ratio RUS | | | | | | | | | |
| Pre-IX Vickers Crack Initiation Load | | | | | | | | | |

TABLE 1-continued

| | | | | | | | | | |
|---|---|---|---|---|---|---|---|---|---|
| (gf) | | | | | | | | | |
| DSC Glass Transition Temperature (° C.) | | | | | | | | | |
| CTE (10^-7) (1/K) | | | | | | | | | |
| Liquidus Temperature (° C.) | | | 790 | | | | | | |

| Example | 28 | 29 | 30 | 31 | 32 | 33 | 34 | 35 | 36 |
|---|---|---|---|---|---|---|---|---|---|
| SiO$_2$ mol % | 60 | 60 | 60 | 56 | 58 | 61 | 59 | 57 | 62 |
| B$_2$O$_3$ | 4.5 | 4.5 | 4.5 | 3.5 | 3 | 0 | 0 | 0 | 0 |
| Al$_2$O$_3$ | 15.4 | 15.4 | 15.4 | 17 | 16.5 | 15.5 | 16.5 | 17.5 | 15.5 |
| P$_2$O$_5$ | 4 | 4 | 4 | 4 | 4 | 7 | 7 | 7 | 6 |
| Na$_2$O | 15.5 | 16 | 15.5 | 19.5 | 18.5 | 16.5 | 17.6 | 18.5 | 16.5 |
| K$_2$O | 0.5 | 0 | 0.5 | 0 | 0 | 0 | 0 | 0 | 0 |
| As$_2$O$_3$ | 0 | 0 | 0 | 0 | 0 | 0 | 0 | 0 | 0 |
| Cs$_2$O | 0 | 0 | 0 | 0 | 0 | 0 | 0 | 0 | 0 |
| Li$_2$O | 0 | 0 | 0 | 0 | 0 | 0 | 0 | 0 | 0 |
| MgO | 0 | 0 | 0 | 0 | 0 | 0 | 0 | 0 | 0 |
| ZnO | 0 | 0 | 0 | 0 | 0 | 0 | 0 | 0 | 0 |
| SnO$_2$ | 0.1 | 0.1 | 0.1 | 0 | 0 | 0 | 0 | 0 | 0 |
| ZrO$_2$ | 0 | 0 | 0 | 0 | 0 | 0 | 0 | 0 | 0 |
| CaO | | | | 0 | 0 | 0 | 0 | 0 | 0 |
| P$_2$O$_5$ + R$_2$O/ Al$_2$O$_3$ + B$_2$O$_3$ | 1.00503 | 1.00503 | 1.00503 | 1.14634 | 1.15385 | 1.51613 | 1.48485 | 1.45714 | 1.45161 |
| Al$_2$O$_3$ + B$_2$O$_3$/ R$_2$O | 1.24375 | 1.24375 | 1.24375 | 1.05128 | 1.05405 | 0.93939 | 0.94286 | 0.94595 | 0.93939 |
| Density (g/cm$^3$) Archimedes | 2.388 | 2.388 | 2.388 | 2.42 | 2.414 | 2.388 | 2.401 | 2.412 | 2.393 |
| Molar Volume (cm$^3$/mol) | 29.63 | 29.56 | 29.63 | 29.41 | 29.37 | 30.41 | 30.43 | 30.47 | 30.01 |
| Calc Young's Modulus (GPa) Makashima MacKenzie | | | | | | | | | |
| Young's Modulus RUS (GPa) | | | 63.4 | | | | | | |
| Shear Mudulus RUS (GPa) | | | 25.1 | | | | | | |
| Poissons Ratio RUS | | | 0.215 | | | | | | |
| Pre-IX Vickers Crack Initiation Load (gf) | | | | | | | | | |
| DSC Glass Transition Temperature (° C.) | | | | | | | | | |
| CTE (10^-7) (1/K) | | | | | | | | | |
| Liquidus Temperature (° C.) | 785 | 790 | 730 | 740 | 790 | 775 | 740 | 730 | 770 |

| Example | 37 | 38 | 39 | 40 | 41 | 42 | 43 | 44 | 45 |
|---|---|---|---|---|---|---|---|---|---|
| SiO$_2$ mol % | 60 | 58 | 58.8 | 58.8 | 60 | 60 | 60 | 55 | 55 |
| B$_2$O$_3$ | 0 | 0 | 4 | 4 | 4 | 4 | 5 | 5 | 0 |
| Al$_2$O$_3$ | 16.5 | 17.5 | 16.3 | 16.3 | 15.75 | 15.75 | 14 | 14 | 15 |
| P$_2$O$_5$ | 6 | 6 | 4 | 4 | 4 | 4 | 5 | 5 | 5 |
| Na$_2$O | 17.5 | 18.5 | 16.4 | 16.9 | 15.75 | 16.25 | 13 | 14 | 15 |
| K$_2$O | 0 | 0 | 0.5 | 0 | 0.5 | 0 | 3 | 2 | 10 |
| As$_2$O$_3$ | 0 | 0 | 0 | 0 | 0 | 0 | 0 | 0 | 0 |
| Cs$_2$O | 0 | 0 | 0 | 0 | 0 | 0 | 0 | 0 | 0 |
| Li$_2$O | 0 | 0 | 0 | 0 | 0 | 0 | 0 | 0 | 0 |
| MgO | 0 | 0 | 0 | 0 | 0 | 0 | 0 | 0 | 0 |
| ZnO | 0 | 0 | 0 | 0 | 0 | 0 | 0 | 0 | 0 |
| SnO$_2$ | 0 | 0 | 0 | 0 | 0 | 0 | 0 | 0 | 0 |
| ZrO$_2$ | 0 | 0 | 0 | 0 | 0 | 0 | 0 | 0 | 0 |
| CaO | 0 | 0 | 0 | 0 | 0 | 0 | 0 | 0 | 0 |
| P$_2$O$_5$ + R$_2$O/ Al$_2$O$_3$ + B$_2$O$_3$ | 1.42424 | 1.4 | 1.02956 | 1.02956 | 1.02532 | 1.02532 | | | |

TABLE 1-continued

|  |  |  |  |  |  |  |
|---|---|---|---|---|---|---|
| $Al_2O_3 + B_2O_3/$<br>$R_2O$ | 0.94286 | 0.94595 | 1.20118 | 1.21539 | 1.21539 | 1.21539 |
| Density<br>$(g/cm^3)$<br>Archimedes | 2.406 | 2.416 | 2.395 | 2.394 | 2.389 | 2.388 |
| Molar Volume<br>$(cm^3/mol)$ | 30.03 | 30.08 | 29.67 | 29.61 | 29.64 | 29.58 |
| Calc Young's<br>Modulus (GPa)<br>Makashima<br>MacKenzie |  |  |  |  |  |  |
| Young's<br>Modulus RUS<br>(GPa) |  |  |  |  |  |  |
| Shear<br>Mudulus RUS<br>(GPa) |  |  |  |  |  |  |
| Poissons<br>Ratio RUS |  |  |  |  |  |  |
| Pre-IX Vickers<br>Crack<br>Initiation Load<br>(gf) |  |  |  |  |  |  |
| DSC Glass<br>Transition<br>Temperature<br>(° C.) |  |  |  |  |  |  |
| CTE ($10^{-7}$)<br>(1/K) |  |  |  |  |  |  |
| Liquidus<br>Temperature<br>(° C.) | 790 | 770 |  |  |  |  |

| Example | 46 | 47 | 48 | 49 | 50 | 51 | 52 | 53 | 54 |
|---|---|---|---|---|---|---|---|---|---|
| $SiO_2$ mol % | 57.9 | 57.9 | 58 | 58 | 58 | 56 | 54 | 52 | 60 |
| $B_2O_3$ | 5.25 | 5.25 | 5 | 5 | 5 | 6 | 7 | 8 | 0 |
| $Al_2O_3$ | 15.5 | 15.5 | 16 | 15.75 | 15.75 | 16 | 16 | 16 | 16 |
| $P_2O_5$ | 5.25 | 5.25 | 5 | 5 | 5 | 6 | 7 | 8 | 5 |
| $Na_2O$ | 14 | 14 | 14 | 13.75 | 13.75 | 14 | 14 | 14 | 16 |
| $K_2O$ | 2 | 2 | 2 | 2 | 2 | 2 | 2 | 2 | 0 |
| $As_2O_3$ | 0 | 0 | 0 | 0 | 0 | 0 | 0 | 0 | 0 |
| $Cs_2O$ | 0 | 0 | 0 | 0 | 0 | 0 | 0 | 0 | 0 |
| $Li_2O$ | 0 | 0 | 0 | 0 | 0 | 0 | 0 | 0 | 0 |
| MgO | 0 | 0 | 0 | 0.5 | 0 | 0 | 0 | 0 | 3 |
| ZnO | 0 | 0 | 0 | 0 | 0.5 | 0 | 0 | 0 | 0 |
| $SnO_2$ | 0.1 | 0.1 | 0 | 0 | 0 | 0 | 0 | 0 | 0 |
| $ZrO_2$ | 0 | 0 | 0 | 0 | 0 | 0 | 0 | 0 | 0 |
| CaO | 0 | 0 | 0 | 0 | 0 | 0 | 0 | 0 | 0 |
| $P_2O_5 + R_2O/$<br>$Al_2O_3 + B_2O_3$ |  |  |  |  |  |  |  |  |  |
| $Al_2O_3 + B_2O_3/$<br>$R_2O$ |  |  |  |  |  |  |  |  |  |
| Density<br>$(g/cm^3)$<br>Archimedes |  | 2.381 | 2.379 | 2.381 | 2.387 | 2.373 | 2.369 | 2.363 | 2.417 |
| Molar Volume<br>$(cm^3/mol)$ |  | 30.35 |  |  |  | 30.85 | 31.29 | 31.76 | 29.21 |
| Calc Young's<br>Modulus (GPa)<br>Makashima<br>MacKenzie |  |  |  |  |  |  |  |  |  |
| Young's<br>Modulus RUS<br>(GPa) |  |  |  |  |  |  |  |  |  |
| Shear<br>Mudulus RUS<br>(GPa) |  |  |  |  |  |  |  |  |  |
| Poissons<br>Ratio RUS |  |  |  |  |  |  |  |  |  |
| Pre-IX Vickers<br>Crack<br>Initiation Load<br>(gf) |  |  |  |  |  |  |  |  |  |
| DSC Glass<br>Transition<br>Temperature<br>(° C.) |  |  |  |  |  |  |  |  |  |
| CTE ($10^{-7}$)<br>(1/K) |  |  |  |  |  |  |  |  |  |

TABLE 1-continued

| Liquidus Temperature (° C.) | 730 | | 730 | 785 | 800 | 775 | 765 | 790 | 960 |
|---|---|---|---|---|---|---|---|---|---|

| Example | 55 | 56 | 57 | 58 | 59 | 60 | 61 | 62 | 63 |
|---|---|---|---|---|---|---|---|---|---|
| SiO$_2$ mol % | 60 | 60 | 60 | 60 | 60 | 62 | 62.5 | 63 | 63.5 |
| B$_2$O$_3$ | 0 | 0 | 0 | 0 | 0 | 0 | 0 | 0 | 0 |
| Al$_2$O$_3$ | 16 | 16 | 16 | 16 | 16 | 15 | 15 | 14.5 | 14.5 |
| P$_2$O$_5$ | 5 | 6 | 6 | 7 | 7 | 5 | 5 | 5 | 5 |
| Na$_2$O | 16 | 16 | 16 | 16 | 16 | 15 | 15 | 14.5 | 14.5 |
| K$_2$O | 0 | 0 | 0 | 0 | 0 | 0 | 0 | 0 | 0 |
| As$_2$O$_3$ | 0 | 0 | 0 | 0 | 0 | 0 | 0 | 0 | 0 |
| Cs$_2$O | 0 | 0 | 0 | 0 | 0 | 0 | 0 | 0 | 0 |
| Li$_2$O | 0 | 0 | 0 | 0 | 0 | 0 | 0 | 0 | 0 |
| MgO | 0 | 2 | 0 | 1 | 0 | 3 | 2.5 | 3 | 2.5 |
| ZnO | 3 | 0 | 2 | 0 | 1 | 0 | 0 | 0 | 0 |
| SnO$_2$ | 0 | 0 | 0 | 0 | 0 | 0 | 0 | 0 | 0 |
| ZrO$_2$ | 0 | 0 | 0 | 0 | 0 | 0 | 0 | 0 | 0 |
| CaO | 0 | 0 | 0 | 0 | 0 | 0 | 0 | 0 | 0 |
| P$_2$O$_5$ + R$_2$O/ Al$_2$O$_3$ + B$_2$O$_3$ | | | | | | | | | |
| Al$_2$O$_3$ + B$_2$O$_3$/ R$_2$O | | | | | | | | | |
| Density (g/cm$^3$) Archimedes | 2.453 | 2.406 | 2.428 | 2.393 | 2.404 | | | | |
| Molar Volume (cm$^3$/mol) | 29.28 | 29.76 | 29.83 | 30.35 | 30.38 | | | | |
| Calc Young's Modulus (GPa) Makashima MacKenzie | | | | | | | | | |
| Young's Modulus RUS (GPa) | | | | | | | | | |
| Shear Mudulus RUS (GPa) | | | | | | | | | |
| Poissons Ratio RUS | | | | | | | | | |
| Pre-IX Vickers Crack Initiation Load (gf) | | | | | | | | | |
| DSC Glass Transition Temperature (° C.) | | | | | | | | | |
| CTE (10$^-7$) (1/K) | | | | | | | | | |
| Liquidus Temperature (° C.) | | | | | | | | | |

| Example | 64 | 65 | 66 | 67 | 68 | 69 | 70 | 71 | 72 |
|---|---|---|---|---|---|---|---|---|---|
| SiO$_2$ mol % | 64 | 64.5 | 62 | 62.5 | 63 | 63.5 | 64 | 64.5 | 60 |
| B$_2$O$_3$ | 0 | 0 | 0 | 0 | 0 | 0 | 0 | 0 | 0 |
| Al$_2$O$_3$ | 14 | 14 | 15 | 15 | 14.5 | 14.5 | 14 | 14 | 15.95 |
| P$_2$O$_5$ | 5 | 5 | 4 | 4 | 4 | 4 | 4 | 4 | 5 |
| Na$_2$O | 14 | 14 | 15 | 15 | 14.5 | 14.5 | 14 | 14 | 15.95 |
| K2O | 0 | 0 | 0 | 0 | 0 | 0 | 0 | 0 | 0 |
| As$_2$O$_3$ | 0 | 0 | 0 | 0 | 0 | 0 | 0 | 0 | 0 |
| Cs$_2$O | 0 | 0 | 0 | 0 | 0 | 0 | 0 | 0 | 0 |
| Li$_2$O | 0 | 0 | 0 | 0 | 0 | 0 | 0 | 0 | 0 |
| MgO | 3 | 2.5 | 4 | 3.5 | 4 | 3.5 | 4 | 3.5 | 3 |
| ZnO | 0 | 0 | 0 | 0 | 0 | 0 | 0 | 0 | 0 |
| SnO$_2$ | 0 | 0 | 0 | 0 | 0 | 0 | 0 | 0 | 0.1 |
| ZrO$_2$ | 0 | 0 | 0 | 0 | 0 | 0 | 0 | 0 | 0 |
| CaO | 0 | 0 | 0 | 0 | 0 | 0 | 0 | 0 | 0 |
| P$_2$O$_5$ + R$_2$O/ Al$_2$O$_3$ + B$_2$O$_3$ | | | | | | | | | |
| Al$_2$O$_3$ + B$_2$O$_3$/ R$_2$O | | | | | | | | | |
| Density (g/cm$^3$) Archimedes | | | | | | | | | |
| Molar Volume (cm$^3$/mol) | | | | | | | | | |

TABLE 1-continued

Calc Young's Modulus (GPa) Makashima MacKenzie
Young's Modulus RUS (GPa)
Shear Mudulus RUS (GPa)
Poissons Ratio RUS
Pre-IX Vickers Crack Initiation Load (gf)
DSC Glass Transition Temperature (° C.)
CTE ($10^{-7}$) (1/K)
Liquidus Temperature (° C.)

| Example | 73 | 74 | 75 | 76 | 77 | 78 | 79 | 80 | 81 |
|---|---|---|---|---|---|---|---|---|---|
| $SiO_2$ mol % | 62 | 63 | 61.5 | 63 | 60.5 | 60.5 | 61 | 61 | 62 |
| $B_2O_3$ | 0 | 0 | 0 | 0 | 0 | 0 | 0 | 0 | 0 |
| $Al_2O_3$ | 14.95 | 14.45 | 15 | 14 | 15.5 | 15.25 | 15.25 | 15 | 14.75 |
| $P_2O_5$ | 5 | 4 | 5 | 5 | 5 | 5 | 5 | 5 | 5 |
| $Na_2O$ | 14.95 | 14.45 | 15 | 14 | 15.5 | 15.25 | 15.25 | 15 | 14.75 |
| $K_2O$ | 0 | 0 | 0 | 0 | 0 | 0 | 0 | 0 | 0 |
| $As_2O_3$ | 0 | 0 | 0 | 0 | 0 | 0 | 0 | 0 | 0 |
| $Cs_2O$ | 0 | 0 | 0 | 0 | 0 | 0 | 0 | 0 | 0 |
| $Li_2O$ | 0 | 0 | 0 | 0 | 0 | 0 | 0 | 0 | 0 |
| MgO | 3 | 4 | 3.5 | 4 | 3.5 | 4 | 3.5 | 4 | 3.5 |
| ZnO | 0 | 0 | 0 | 0 | 0 | 0 | 0 | 0 | 0 |
| $SnO_2$ | 0.1 | 0.1 | 0 | 0 | 0 | 0 | 0 | 0 | 0 |
| $ZrO_2$ | 0 | 0 | 0 | 0 | 0 | 0 | 0 | 0 | 0 |
| CaO | 0 | 0 | 0 | 0 | 0 | 0 | 0 | 0 | 0 |
| $P_2O_5 + R_2O/Al_2O_3 + B_2O_3$ | | | | | | | | | |
| $Al_2O_3 + B_2O_3/R_2O$ | | | | | | | | | |
| Density (g/cm³) Archimedes | 2.41 | 2.419 | | | 2.417 | | | | |
| Molar Volume (cm³/mol) | | | | | | | | | |
| Calc Young's Modulus (GPa) Makashima MacKenzie | | | | | | | | | |
| Young's Modulus RUS (GPa) | | | | | | | | | |
| Shear Mudulus RUS (GPa) | | | | | | | | | |
| Poissons Ratio RUS | | | | | | | | | |
| Pre-IX Vickers Crack Initiation Load (gf) | | | | | | | | | |
| DSC Glass Transition Temperature (° C.) | | | | | | | | | |
| CTE ($10^{-7}$) (1/K) | | | | | | | | | |
| Liquidus Temperature (° C.) | | | | | | | | | |

TABLE 1-continued

| Example | 82 | 83 | 84 | 85 | 86 | 87 | 88 | 89 | 90 |
|---|---|---|---|---|---|---|---|---|---|
| $SiO_2$ mol % | 62 | 60.5 | 60 | 60.5 | 56 | 58 | 52 | 58 | 59 |
| $B_2O_3$ | 0 | 0 | 0 | 0 | 0 | 0 | 4 | 2 | 1 |
| $Al_2O_3$ | 14.5 | 14.8 | 15.5 | 15.25 | 22 | 21 | 22 | 20 | 20 |
| $P_2O_5$ | 5 | 5 | 5 | 5 | 6 | 5 | 6 | 4 | 4 |
| $Na_2O$ | 14.5 | 15.7 | 16.5 | 15.25 | 14 | 14 | 14 | 14 | 14 |
| $K_2O$ | 0 | 0 | 0 | 0 | 2 | 2 | 2 | 2 | 2 |
| $As_2O_3$ | 0 | 0 | 0 | 0 | 0 | 0 | 0 | 0 | 0 |
| $Cs_2O$ | 0 | 0 | 0 | 0 | 0 | 0 | 0 | 0 | 0 |
| $Li_2O$ | 0 | 0 | 0 | 0 | 0 | 0 | 0 | 0 | 0 |
| MgO | 4 | 4 | 3 | 4 | 0 | 0 | 0 | 0 | 0 |
| ZnO | 0 | 0 | 0 | 0 | 0 | 0 | 0 | 0 | 0 |
| $SnO_2$ | 0 | 0 | 0 | 0 | 0 | 0 | 0 | 0 | 0 |
| $ZrO_2$ | 0 | 0 | 0 | 0 | 0 | 0 | 0 | 0 | 0 |
| CaO | 0 | 0 | 0 | 0 | 0 | 0 | 0 | 0 | 0 |
| $P_2O_5 + R_2O/$ $Al_2O_3 + B_2O_3$ | | | | | | | | | |
| $Al_2O_3 + B_2O_3/$ $R_2O$ | | | | | | | | | |
| Density (g/cm$^3$) Archimedes | | | | | | | | | |
| Molar Volume (cm$^3$/mol) | | | | | | | | | |
| Calc Young's Modulus (GPa) Makashima MacKenzie | | | | | | | | | |
| Young's Modulus RUS (GPa) | | | | | | | | | |
| Shear Mudulus RUS (GPa) | | | | | | | | | |
| Poissons Ratio RUS | | | | | | | | | |
| Pre-IX Vickers Crack Initiation Load (gf) | | | | | | | | | |
| DSC Glass Transition Temperature (° C.) | | | | | | | | | |
| CTE ($10^{-7}$) (1/K) | | | | | | | | | |
| Liquidus Temperature (° C.) | | | | | | | | | |

Glasses according to embodiments disclosed herein may be formed into glass articles, such as, for example, glass sheets. In embodiments, the glass composition has a liquidus viscosity of at least 130 kilopoise and is down-drawable by suitable techniques, for example, but not limited to, fusion-draw processes, slot-draw processes, and re-draw processes. In other embodiments the glass sheet can be made by the float process. Three dimensional glass articles may be made by, for example, molding, blow molding, and the like.

The glass composition may be formed into glass sheets having any thickness. For example, for embodiments used in electronic devices such as touch screens or a touch screen cover glasses for cell phones, computers (including laptops and tablets) and ATMs, the glass sheet may have a thickness in the range of 0.2 mm to 3 mm. In other embodiments the glass sheet may have a thickness in the range of 0.2 mm to 2.0 mm. In further embodiments, the glass sheet may have a thickness in the range of 0.3 mm to 0.7 mm. Other applications of glasses according to embodiments include use as table tops or cover tops, shelving in refrigerators or for storage shelves or shelf covers in, for example, laboratories, hospitals and other facilities where antimicrobial properties are desired. It should be noted that the glass can be thicker according to the intended use. For example, for a hospital bench top or bench top cover, it may be desirable that the glass have a thickness of greater than 3 mm.

Glass Strengthening

According to embodiments, the glass compositions may be strengthened, such as, for example, by physical and/or chemical tempering. In some embodiments, the glass composition may be strengthened by ion exchange. Glass compositions that are amenable to ion exchange typically contain smaller monovalent alkali metal ions, such as, for example, Na and/or Li ions, that can be exchanged by larger monovalent ions, such as, for example, K, Rb, Cs, and/or Ag ions. Exemplary glass compositions that are amenable to ion exchange are discussed above.

Embodiments include strengthening a glass article, such as a glass sheet, in a two-step (2-step) method. The 2-step method of embodiments uses a first ion-exchange bath containing an ion-exchanging alkali metal compound with ions larger than the alkali ions in the glass article (e.g., exchanging Na ions in the glass article for K ions in an ion-exchange bath), followed by ion-exchange using a second ion-exchange bath containing an anti-microbial agent such as silver. In some embodiments, the glass article may be exposed to the silver-containing ion-exchange bath for a much shorter time than the first ion-exchange bath. The silver ion-exchange bath may contain a high concentration of both silver ions and, optionally, an ion-exchanging alkali metal compound whose ions are larger than the alkali metal ions in the glass article.

In a first step of a 2-step method according to embodiments, the larger alkali metal ions are exchanged into the glass to form a glass article having a compressive stress. In embodiments, the glass article may be exposed to the ion-exchange bath for a time greater than or equal to about 3 hours at a temperature from greater than or equal to about 300° C. to less than or equal to about 500° C. In some embodiments, the glass article may be exposed to the ion-exchange bath at a temperature of from greater than or equal to about 350° C. to less than or equal to about 450° C. and for a duration of from greater than or equal to about 40 minutes to less than or equal to about 6 hours, such as from greater than or equal to about 1.0 hour to less than or equal to about 5 hours. This first step increases the compressive stress of the glass article by replacing smaller ions in the glass matrix, such as Na ions, with larger ions, such as, for example, K ions. In embodiments, the ion-exchange bath for the first step of the 2-step method may include one or more of $NaNO_3$ and $KNO_3$. In some embodiments, the ion-exchange bath for the first step of the 2-step method may be $KNO_3$. Suitable ion exchange processes for the first step of the 2-step method are disclosed in U.S. Pat. No. 5,674,790, which is herein incorporated by reference in its entirety.

In the second step of the 2-step ion exchange method, silver ions are exchanged into the surface of the glass article and replace the alkali metal ions in the glass to a shallow enough depth so that there is not significant loss or relaxation of the compressive stress which was increased during the first step of the ion exchange process. In embodiments, the ion-exchange bath of the second step may primarily comprise Ag-containing compounds, such as, for example $AgNO_3$. In other embodiments of the 2-step method, the second step may include alkali metal containing compounds in addition to Ag-containing compounds. In embodiments, the same alkali metal containing compound may be used in both the first and second ion-exchange baths. Thus, in some embodiments, the second step of the 2-step method includes exposing the glass article to an ion exchange bath comprising $AgNO_3$ and $KNO_3$.

The ion-exchange bath in the second step of the 2-step method may, in embodiments, include from greater than or equal to about 5.0 mol. % to less than or equal to 100 mol. % Ag-containing compounds, such as, for example, $AgNO_3$. In some embodiments, the second step of the 2-step method may include from greater than or equal to about 10 mol. % to less than or equal to 95 mol. % Ag-containing compounds, such as from greater than or equal to about 15 mol. % to less than or equal to about 90 mol. % Ag-containing compounds. In other embodiments, the second step of the 2-step method may include from greater than or equal to about 20 mol. % to less than or equal to 85 mol. % Ag-containing compounds, such as from greater than or equal to about 25 mol. % to less than or equal to about 80 mol. % Ag-containing compounds. In yet other embodiments, the second step of the 2-step method may include from greater than or equal to about 30 mol. % to less than or equal to 75 mol. % Ag-containing compounds, such as from greater than or equal to about 35 mol. % to less than or equal to about 70 mol. % Ag-containing compounds. In each of the above embodiments, the remainder of the ion-exchange bath composition may be one or more alkali metal compounds, such as, for example, $KNO_3$ and/or $NaNO_3$.

In embodiments, the duration of the ion-exchange time using the silver-containing bath may be less than or equal to about 30 minutes, which may produce a shallow depth of exchange, such as less than 20 μm. In some embodiments the ion-exchange time is from greater than or equal to 0.0 minutes to less than or equal to about 20 minutes. In other embodiments, the ion-exchange time is from greater than or equal to 0.0 minutes to less than or equal to about 10 minutes. The ion-exchange is carried out at a temperature from greater than or equal to about 370° C. to less than or equal to about 450° C., such as at a temperature from greater than or equal to about 400° C. to less than or equal to about 440° C. Without being bound to any specific theory, the 2-step method of ion exchange provides the glass with only a surface concentration of $Ag^{+1}$ to facilitate the antimicrobial effect as having the silver penetrate to greater depths adds nothing to the antimicrobial or antibacterial effect since silver ions do not move or migrate within the glass at the typical end-use application temperatures. The 2-step method thus allows one to obtain a significantly higher concentration of $Ag^{+1}$ ions on the surface of the glass which results in a commensurate decrease in the "kill" time (the time to reach a log 3 reduction in microbes) while not producing any undesirable yellow color or decreasing the compressive stress of the glass article by replacing deeply positioned alkali metal ions with smaller Ag ions.

In embodiments, the glass article may have a maximum concentration of Ag ions within 60 nm of a free surface of the glass article, such as within 50 nm of a free surface of the glass article. In other embodiments, the glass article may have a maximum concentration of Ag ions within 40 nm of a free surface of the glass article, such as within 30 nm of the free surface of the glass article. As used herein, "free surface" is used to indicate a surface of the glass article that is exposed and intended to be exposed in the final use of the glass article.

The quantitative knowledge of the surface Ag ion concentration is desired to ascertain the effectiveness of the antimicrobial action. This is even more pertinent in the present case where the Ag is being added by an ion-exchange process. In embodiments, the glass article may comprise an average concentration of Ag within 60 nm of a free surface of the glass greater than or equal to about 10 mol. % to less than or equal to about 15 mol. %, such as greater than or equal to about 12 mol. % to less than or equal to about 14 mol. %. The analytical techniques XPS (X-ray photoluminescence spectroscopy) and SIMS (secondary ion mass spectroscopy) can be used to obtain the Ag ion profile, but they yield volume concentration values, albeit close to the surface, whereas what is important is the surface ion concentration. XPS can quantitatively determine the Ag ion concentration to within 10-20 nm.

In embodiments, the depth of a compressive stress layer formed by the 2-step ion exchange method may be from greater than or equal to about 20 μm to less than or equal to about 60 μm, such as from greater than or equal to about 25 μm to less than or equal to about 55 μm. In other embodiments, the depth of a compressive stress layer formed by the 2-step ion exchange method may be from greater than or equal to about 30 μm to less than or equal to about 50 μm, such as from greater than or equal to about 35 μm to less than or equal to about 45 μm. In yet other embodiments, the depth of a compressive stress layer formed by the 2-step ion exchange method may be from greater than or equal to about 40 μm to less than or equal to about 50 μm. In embodiments, the compressive stress of the glass article formed by the 2-step ion exchange method may be greater than or equal to about 700 MPa, such as greater than or equal to about 800 MPa. In other embodiments, the compressive stress of the glass article formed by the 2-step method may be greater than or equal to about 900 MPa. In embodiments, the compressive stress of the glass article formed by the 2-step ion exchange method may be less than or equal to about 1100 MPa.

Without being bound to any particularly theory, it is believed that there is minimal impact on the compressive stress using the 2-step method, because the depth of the Ag ion exchange into the glass in the second step is shallow. Therefore, the compressive stress of the glass, which was chemically strengthened in a first step by ion-exchange of larger ions, such as, for example K or larger alkali metal ions, for smaller ions in the glass, such as, for example, Na and/or Li ions, the compressive stress of the glass is not measurably affected. Further, it is noted that the ionic radius of silver and potassium ions are similar, the Pauling ionic radii of silver and potassium being 1.26 and 1.33 Angstroms, respectively. Consequently, an ion-exchange of silver ions for potassium ions already in the glass after the first step ion-exchange will have a minimal effect on the compressive stress of the glass.

In embodiments, the glass may have a light transmission, uncorrected for reflection losses, over wavelengths from greater than or equal to about 400 nm to less than or equal to about 750 nm, of greater than or equal to about 85%. In some embodiments, the glass may have a light transmission, uncorrected for reflection losses, over wavelengths from greater than or equal to about 400 nm to less than or equal to about 750 nm, from greater than or equal to about 85% to less than or equal to about 92%, such as from greater than or equal to about 88% to less than or equal to about 90%.

Antimicrobial Efficacy

As used herein the term "antimicrobial," means an agent or material, or a surface containing the agent or material that will kill or inhibit the growth of microbes from at least two of the families consisting of bacteria, viruses, and fungi. The term as used herein does not mean it will kill or inhibit the growth of all microbe species within such families, but that it will kill or inhibit the growth or one or more species of microbes from such families.

As used herein the term "Log Kill" means $-\text{Log}(C_a/C_0)$, where $C_a$=the colony form unit (CFU) number of the antimicrobial surface containing silver ions and $C_0$=the colony form unit (CFU) of the control glass surface that does not contain silver ions. That is:

$$\text{Log Kill} = -\text{Log}(C_a/C_0).$$

As an example, a Log Kill of 4=99.99% of the bacteria or virus killed and a Log Kill of 6=99.9999% of bacteria or virus killed.

According to embodiments, the antimicrobial activity of the glass articles when measured at high relative humidity (RH), such as, for example, RH greater than or equal to about 90%, and physiological temperatures, such as, about 37° C., when measured using JIS Z International Test, are greater than or equal to about 5 Log Kill, such as greater than or equal to about 6 Log Kill.

Glass articles according to this disclosure not only have antimicrobial activity at high temperatures and relative humidity, but also have antimicrobial activity at ambient conditions. The antimicrobial activity of glass articles according to embodiments measured at room temperature (i.e., about 23° C.) and low relative humidity (i.e., about 40%) measured according to the EPA testing protocol may be greater than or equal to about 1.0 Log Kill, such as greater than or equal to about 1.2 Log Kill. In some embodiments, the antimicrobial activity of glass articles may be greater than or equal to about 1.4 Log Kill, such as greater than or equal to about 1.6 Log Kill. In other embodiments, the antimicrobial activity may be greater than or equal to about 1.8 Log Kill.

Coatings

Embodiments may include a functional coating on the antimicrobial, chemically strengthened glass. For example, in many touch screen applications (phones, computers, ATMs, etc) where the glass is used as a cover glass, a coating or film is placed on the glass surface so that fingerprints can be cleaned relatively easily. The coating(s) that facilitate cleaning are low surface energy coatings. In embodiments, the coatings may include fluoroalkylsilanes coatings having a general formula $A_x$-Si—$B_{4-x}$, where: A is selected from the group consisting of perfluoroalkyl $R_F$—, perfluoroalkyl terminated perfluoropolyether, perfluoroalkyl-alkyl, copolymers of fluoroalkene silanes and alkene silanes, and mixtures of fluoroalkylsilanes and hydrophilic silanes; B is Cl, acetoxy [$CH_3$—C(O)—O—] or alkoxy [for example $CH_3O$— or $C_2H_5O$—]; and x=1 or 2. Low surface energy coatings of the foregoing types are commercially available from different manufacturers, for example, Dow Corning, [DC2634—a perfluoropolyether silane in which the functional perfluoro moiety is Poly[oxy(1,1,2,2,3,3-hexafluoro-1,3-propanediyl)], a-(heptafluoropropyl)-ω-[1,1,2,2-tetrafluoro-3-(2-propenyloxy)propoxy]; Gelest [SIT8174.0, Tridecafluorotetrahydrooctyltrichlorosilane; SIT8371.0, Trifluoropropyltrichlorosilane; SIH5841.0 Heptadecafluorotetrahydrodecyl trichlorosilane; and SIH5841.0 (heptadecafluoro-1,1,2,2-tetrahydrodecyl)trichlorosilane; SIH58410.5 (heptadecafluoro-1,1,2,2-tetrahydrodecyl)trimethoxysilane; and SIH5841.2 (heptadecafluoro-1,1,2,2-tetrahydrodecyl) triethoxysilane]; Cytonix [FSM 1200 Perfluoropolyether mono-silane; FSD 2500 Medium molecular weight perfluoropolyether di-silane; FSD 4500 High molecular weight perfluoropolyether polysilanes]. The low surface energy coating may have a spacer or skeletal chain length in from greater than or equal to about 1 nm to less than or equal to about 20 nm, the skeletal chain being carbon atoms or a mixture of carbon and oxygen atoms in the case of the perfluoropolyethers. In some embodiments the chain length is from greater than or equal to about 2 nm to less than or equal to about 15 nm. In other embodiment the chain length is from greater than or equal to about 3 nm to less than or equal to about 10 nm.

Other examples of low surface energy coatings are (a) copolymers of fluoroalkene silanes and alkene silanes; and (b) mixtures of fluoroalkylsilanes and hydrophilic silanes.

In embodiments, silanes other than the foregoing can also be used provided that they do not prevent water vapor from reaching the surface of the glass so that silver ions can be transported from the glass surface to the microbe to thereby kill the microbe or inhibit its growth.

Generally, embodiments of the fluoro-containing coatings describe above have 1 or 2 fluorocarbon-containing moieties attached to the silicon and each of the moieties, independently, have a chain length in the range of 1 nm to 20 nm. In embodiments, the chain may include oxygen atoms or sulphur atoms. In embodiments, the chain length may be from greater than or equal to about 1 nm to less than or equal to about 20 nm, such as from greater than or equal to about 2 nm to less than or equal to about 10 nm. According to some embodiments, at least part the fluorocarbon moiety be sufficiently distant from the surface so that water molecules can come into contact with the surface, pick up silver ions on the surface, and transport the silver ions to a microbe where they can be absorbed in to microbe and thus kill it or decrease its reproductive rate. Consequently, it is preferred that one or two fluorocarbon moieties be attached to the silicon atom and that the silicon atom be bonded to the glass by two or three Si—O bonds. For example, if the alkyl group of (a) above, which functions as a spacer or skeletal chain between the silver-containing glass surface and the fluorocarbon moiety, is too short, then a hydrophobic fluorocarbon moiety can block water molecules from reaching the glass surface and thus silver ions cannot be transported from the surface to and into the microbe. In another instance, without being constrained by any particular theory, it is believed that the oxygen atoms in a perfluoropolyether alkoxy silane that has been bonded to the surface of the antimicrobial glass can facilitate the migration of water molecules by oxygen atoms along the chain to the surface where the water molecules can coordinate to silver ions and facilitate the ion transport to the microbe. An exemplary perfluoropolyether alkoxy silane is Dow Corning® 2634 used as 0.02-1 wt % solutions in a fluorinated solvent. After the coating material was applied to the antimicrobial glass article such as described herein, the coating was cured to adhere the coating to the surface of the glass article and finally sonicated in a fluorinated solvent (for example, Novec™ HFE7200, 3M Company) bath for a 3 minutes remove any unreacted coating material. The curing was done thermally by either heating the coated articles in an oven, for example, at 50° C., 50% RH, for a cure time as suggested by the manufacturer or by infrared heating of the coated articles. The coated article was then heated in an oven for a time in the range of 30 minutes to 2 hours to cure the coating material to the glass surface.

The method and process for the deposition of these coatings are capable of controlling the thickness and morphology of the coating on the surface of the glass. Process methods and steps can be introduced where the coating was deposited in such a fashion either to be discontinuous or quasi-discontinuous. Such process methods include, but are not limited to, vapor deposition or spray coating through a predetermined coverage mask, ink jet printing, micro contact printing using a master which would allow the fluorosilane to be coated in specific regions, and humidity curing to allow phase separation of the fluorosilane. When the coating is sufficiently thin it can be continuous. Thin continuous coatings can be deposited, for example, by dip, spray and vapor deposition followed by curing to adhere the silanes, and followed by ultrasound cleaning to remove un-reacted but physically adsorbed silanes. The foregoing procedures allow the antimicrobial action to persist in open uncoated areas, or in areas where the coating is very thin or the surface is coating-free while at the same time maintaining intended functional performance of the coating. In embodiments, the thickness of the coating is from greater than or equal to about 0.5 nm to less than or equal to about 5 nm. In other embodiments the thickness of the coating is from greater than or equal to about 1 nm to less than or equal to about 3 nm. In the thin coating case a mixed self-assembled monolayer can be prepared on the surface using two silanes, where one silane is a fluoroalkylsilane and the other silane is a hydrophilic silane (for example, a polyethylene glycol containing silane), wherein the hydrophilic or "water loving" silane domains assist in the antimicrobial action by capturing water molecules and presenting them to the surface where the water can pick up silver ions for transport to the microbe. In one embodiment fluoro-oligoethylene glycol silanes can also be used, where the oligoethylene glycol part of the silanes can assist in capturing free water at the interface.

EXAMPLES

Embodiments will be further clarified by the following examples.

Example 1

Example 1 tests the strength of five glass samples with a ring-on-ring test. All five glass samples are 1.0 mm thick glass sheets made from Corning 5318 glass. For Comparative Sample 1, the glass is prepared using a one-step ion exchange method with a $KNO_3$ bath. Samples 1-4 are prepared using a 2-step ion exchange method first using a $KNO_3$ bath, followed by a bath of $KNO_3$ and $AgNO_3$.

Figure 1:
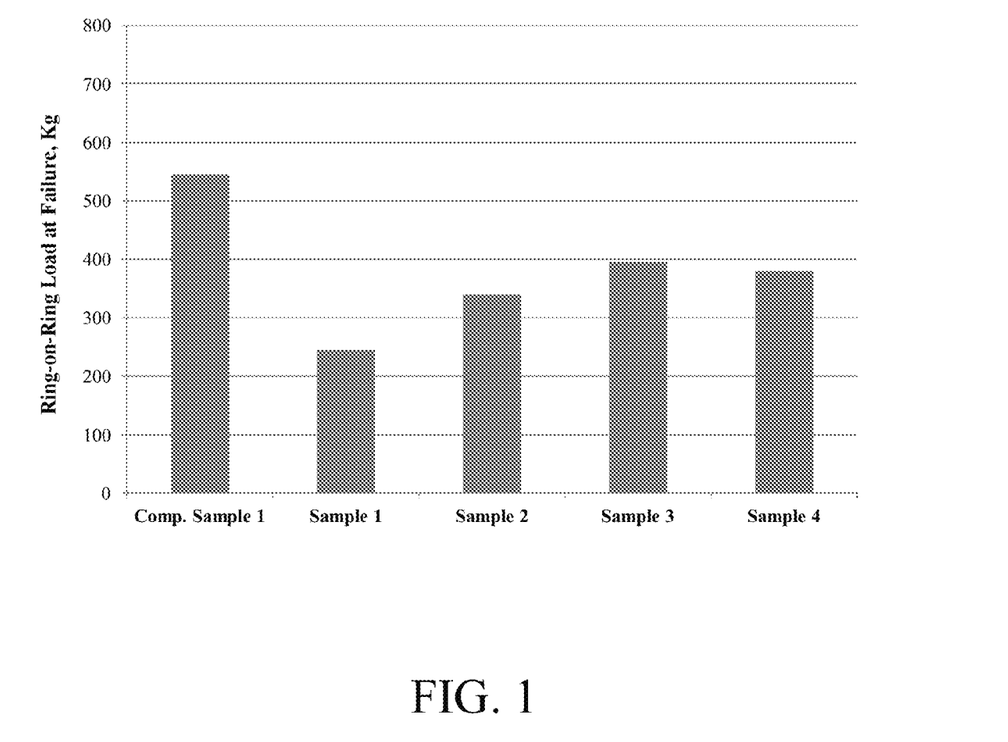
FIG. 1 is a bar graph showing results of a ring-on-ring test for glass articles according to embodiments disclosed herein.

As shown in FIG. 1, Comparative Sample 1, which is prepared using a one-step ion exchange, fails at a load of approximately 525 kg. Samples 1-4, which are prepared using a 2-step ion exchange comprising Ag ions, fail at loads from approximately 250 Kg to approximately 475 Kg. Thus, the samples show that glasses prepared using a 2-step ion exchange method can be prepared to have strengths approximately equal to glasses prepared using a one-step ion exchange method. This was previously unexpected because replacing large alkali metal ions, such as $K^+$, with Ag ions, as is done in the second step of the 2-step ion exchange method, was traditionally thought to lower the strength of the glass article.

Example 2

Example 2 tests antimicrobial activity of three glass samples. All three glass samples are 1.0 mm thick Corning 5318 glass sheets. All three glass samples are ion exchanged in a $KNO_3$ molten salt bath at 420° C. for 2.5 hours. Subsequently, the three glass samples are subjected to a second ion exchange in an ion exchange bath comprising Ag. Comparative Sample 2 is subjected to a 20% Ag and 80% $KNO_3$ ion exchange bath. Sample 5 is subjected to a 100% Ag/K ion exchange bath. Sample 6 is subjected to a 100% Ag/K ion exchange bath.

Figure 2:
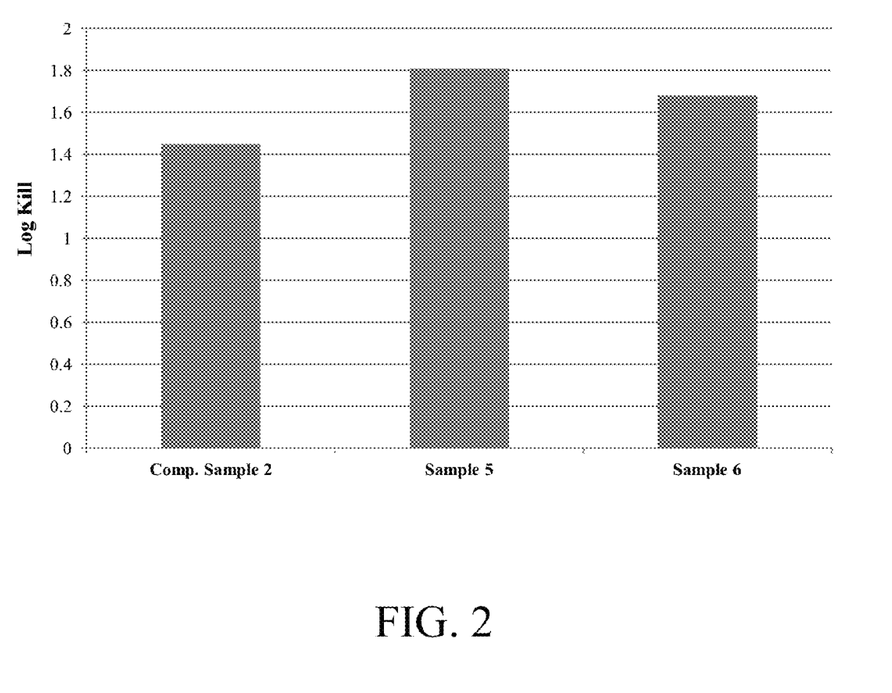
FIG. 2 is a bar graph showing antimicrobial properties of glass articles according to embodiments disclosed herein.

As shown in FIG. 2, Comparative Sample 2 has a Log Kill of about 1.4, Sample 5 has a Log Kill of about 1.8, and Sample 6 has a Log Kill of about 1.6. Thus, these glass samples show that 100% Ag/K ion exchange baths provide better antimicrobial protection at low relative humidity and temperature than 20% Ag ion exchange baths.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:
1. A strengthened antimicrobial glass comprising:
greater than or equal to about 50.0 mol. % to less than or equal to about 65.0 mol. % $SiO_2$;
greater than or equal to about 14.0 mol. % to less than or equal to about 22.0 mol. % $Al_2O_3$;

greater than or equal to about 14.0 mol. % to less than or equal to about 22.0 mol. % $R_2O$, wherein R is an alkali metal; and greater than or equal to about 4.0 mol. % to less than or equal to about 10.0 mol. % $P_2O_5$, wherein:

the glass comprises a compressive stress layer having a thickness of greater than or equal to about 20 μm and having a surface compressive stress of greater than or equal to about 700 MPa; and the glass as an antimicrobial activity greater than or equal to about 1.0 Log Kill at about 23° C. and about 40.0% relative humidity.

2. The glass of claim 1, wherein the glass comprises Ag.

3. The glass of claim 2, wherein the glass has a maximum concentration of Ag within 60 nm of a free surface of the glass.

4. The glass of claim 2, wherein an average concentration of Ag within 60 nm of a free surface of the glass is greater than or equal to about 10 mol. % to less than or equal to about 15 mol. %.

5. The glass of claim 2, wherein the glass has a light transmission of greater than or equal to about 85% over wavelengths from greater than or equal to about 400 nm to less than or equal to about 750 nm.

6. The glass of claim 1, wherein the glass has a molar ratio of $Al_2O_3$ to $R_2O$ that is greater than or equal to about 0.5:1 to less than or equal to about 1.5:1.

7. The glass of claim 1, wherein the glass further comprises greater than 0.0 mol. % to less than or equal to about 4.0 mol. % ZnO.

8. The glass of claim 1, wherein the glass has an antimicrobial activity greater than or equal to about 5.0 Log Kill at about 37° C. and a relative humidity greater than or equal to about 90%.

9. The glass of claim 1, wherein R is selected from the group consisting of Li, Na, and K.

10. The glass of claim 1, wherein the compressive stress layer has a depth greater than or equal to about 40 μm to less than or equal to about 50 μm.

11. The glass of claim 10, wherein the glass has a compressive stress of greater than or equal to about 900 MPa.

12. The glass of claim 1, further comprising greater than 0.0 mol. % to less than or equal to about 4.0 mol. % alkaline earth metal.

13. The glass of claim 1, further comprising a fluorosilane coating on a free surface of the glass.

14. The glass of claim 13, wherein the coating has a general formula of:

$A_x$-Si—$B_{4-x}$, where

A is selected from the group consisting of perfluoroalkyl, perfluoroalkyl terminated perfluoropolyether, perfluoroalkyl-alkyl, copolymers of fluoroalkene silanes and alkene silanes, and mixtures of fluoroalkylsilanes and hydrophilic silanes; and B is selected from the group consisting of Cl, acetoxy, and alkoxy; and x=1 or 2.

15. A method for making strengthened antimicrobial glass, the method comprising:

obtaining a glass article comprising:

greater than or equal to about 50.0 mol. % to less than or equal to about 65.0 mol. % $SiO_2$, greater than or equal to about 14.0 mol. % to less than or equal to about 22.0 mol. % $Al_2O_3$, greater than or equal to about 14.0 mol. % to less than or equal to about 22.0 mol. % $R_2O$, wherein R is an alkali metal, and greater than or equal to about 4.0 mol. % to less than or equal to about 10.0 mol. % $P_2O_5$;

strengthening the glass article by contact with a first ion-exchange liquid; and contacting the glass article with a second ion-exchange liquid comprising an antimicrobial agent, wherein:

the glass comprises a compressive stress layer having a thickness of greater than or equal to about 20 μm to less than or equal to about 60 μm and having a compressive stress of greater than or equal to about 700 MPa; and the glass has an antimicrobial activity greater than or equal to about 1.0 log kill at about 23° C. and a relative humidity of about 40%.

16. The method of claim 15, wherein the first ion-exchange liquid is selected from the group consisting of $NaNO_3$, $KNO_3$, and mixtures thereof.

17. The method of claim 15, wherein the antimicrobial agent comprises Ag.

18. The method of claim 17, wherein the second ion-exchange liquid further comprises a member selected from the group consisting of $NaNO_3$, $KNO_3$, and mixtures thereof.

19. The method of claim 17, wherein a silver salt concentration in the second ion exchange liquid is greater than or equal to about 5.0 mol. %.

20. The method of claim 15, wherein the strengthening step comprises holding the glass article in a bath of the first ion-exchange liquid that has a temperature greater than or equal to about 300° C. to less than or equal to about 500° C. for a duration of greater than or equal to about 40 minutes to less than or equal to about 6 hours.

* * * * *